United States Patent [19]

Fiege et al.

[11] Patent Number: 4,871,484
[45] Date of Patent: Oct. 3, 1989

[54] PROCESS FOR THE PREPARATION OF 2,2-BIS-CHLORO-METHYLALKANECARBOXYLIC ACID CHLORIDES

[75] Inventors: Helmut Fiege, Leverkusen; Manfred Jautelat, Burscheid; Dieter Arlt, Cologne, all of Fed. Rep. of Germany

[73] Assignee: Bayer Aktiengesellschaft, Leverkusen, Fed. Rep. of Germany

[21] Appl. No.: 50,993

[22] Filed: May 15, 1987

[30] Foreign Application Priority Data

May 30, 1986 [DE] Fed. Rep. of Germany ....... 3618142

[51] Int. Cl.4 .......................... C07C 51/58; C09F 7/00
[52] U.S. Cl. ..................................... 260/408; 562/853
[58] Field of Search ........... 260/544 L, 544 D, 544 Y, 260/408

[56] References Cited

FOREIGN PATENT DOCUMENTS 1907117 10/1971 Fed. Rep. of Germany .
0132733 2/1985 Fed. Rep. of Germany .

OTHER PUBLICATIONS

Noller, C. R., Chemistry of Organic Compounds, 2nd. ed. W. B. Saunders Co., Philadelphia, Pa., 1957, p. 246.
Patent Abstracts of Japan, vol. 9, No. 293(C–315, Nov. 20, 1985.

Primary Examiner—Werren B. Lone
Attorney, Agent, or Firm—Sprung Horn Kramer & Woods

[57] ABSTRACT

A process for the preparation of a 2,2-bis-chloro-methyl-alkanecarboxylic acid of the formula

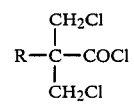

in which R is hydrogen, alkyl, cycloalkyl or optionally substituted phenyl, which comprises reacting an oxetane-3-carboxylic acid of the formula

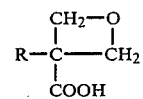

or a salt thereof, with an inorganic acid chloride at a temperature between 20° C. and the boiling point of the reaction mixture. The products are known intermediates for fungicides and herbicides.

4 Claims, No Drawings

PROCESS FOR THE PREPARATION OF 2,2-BIS-CHLORO-METHYLALKANECARBOXYLIC ACID CHLORIDES

The invention relates to a new process for the preparation and of 2,2-bis-chloromethyl-alkanecarboxylic acid chlorides, some of which are known and which can be used as intermediates for the synthesis of substances having fungicidal or herbicidal activity.

It is already known that, in the reaction of 3-alkyloxetane-3-carboxylic acids with thionyl chloride, only the carboxyl group is converted into a chlorocarbonyl group, but the oxetane ring is not changed (cf. German Patent Specification No. 1,907,117). In addition, no reactions are known in which the oxetane ring of oxetane-3-carboxylic acids reacts with thionyl chloride or other inorganic acid chlorides.

It has now been found that 2,2-bis-chloromethylalkanecarboxylic acid chlorides of the formula

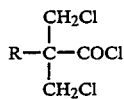  (I)

in which R represents hydrogen, alkyl, cycloalkyl or optionally substituted phenyl,
can be prepared by reacting oxetane-3-carboxylic acids of the formula

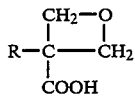  (II)

in which R has the abovementioned meaning,
or salts thereof, with inorganic acid chlorides, if appropriate in the presence of a catalyst and if appropriate in the presence of a diluent, at temperatures between 20° C. and the boiling point of the reaction mixture.

The course of the process according to the invention can be described as extremely surprising. Thus, in view of the known prior art, it could not be presumed that oxetane-3-carboxylic acids of the formula (I) can be converted smoothly into 2,2-bis-chloromethyl-alkanecarboxylic acid chlorides of the formula (I). This is because it was to be expected that such a chlorination only proceeds after prior hydrolytic opening of the oxetane ring.

The process according to the invention is distinguished by a number of advantages. Thus, the starting materials required are readily available, and also in relatively large amounts. Furthermore, the reaction components necessary are inexpensive and easy to handle. It is particularly advantageous that the desired products are produced in very high yield and excellent purity. In addition, the work-up of the reaction mixture present after the reaction presents no difficulties.

If 3-methyl-oxetane-3-carboxylic acid is used as starting material, thionyl chloride as acid chloride and dimethylformamide (=DMF) as catalyst, then the course of the process according to the invention may be illustrated by the following equation:

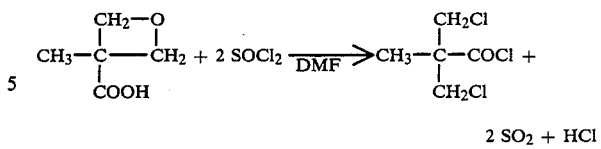

$$2 SO_2 + HCl$$

The oxetane-3-carboxylic acids required as starting materials in the process according to the invention are generally defined by the formula (II). In this formula, R preferably represents hydrogen, alkyl having 1 to 12 carbon atoms, cycloalkyl having 3 to 8 carbon atoms, or phenyl which is optionally substituted by halogen and-/or alkyl having 1 to 6 carbon atoms.

Particularly preferred substances of the formula (II) are those in which R represents hydrogen, alkyl having 1 to 8 carbon atoms, particularly having 1 to 6 carbon atoms, cycloalkyl having 3 to 6 carbon atoms. or phenyl which is optionally substituted by fluorine, chlorine, bromine and/or alkyl having 1 to 4 carbon atoms.

Salts of oxetane-3-carboxylic acids, such as, for example, the alkali metal or alkaline earth metal salts thereof, may also be used preferably. Sodium or potassium salts, and also magnesium or calcium salts, are particularly preferred.

The following may be mentioned as examples of oxetane-3-carboxylic acids of the formula (II):

Oxetane-3-carboxylic acid, 3-methyl-oxetane-3-carboxylic acid, 3-ethyl-oxetane-3-carboxylic acid, 3-propyloxetane-3-carboxylic acid, 3-isopropyloxetane-3-carboxylic acid, 3-butyl-oxetane-3-carboxylic acid, 3-phenyl-oxetane-3-carboxylic acid, 3-cyclohexyl-oxetane-3-carboxylic acid and 3-(4-chlorophenyl)-oxetane-3-carboxylic acid.

Some of the oxetane-3-carboxylic acids of the formula (II) and salts thereof are known. Thus, oxetane-3-carboxylic acids may be prepared by a known process, by dehydrogenating 3-hydroxymethyl-oxetanes in the liquid phase in the presence of catalysts containing copper/chromium/barium at temperatures between 190° and 270° C. The oxetane-3-carboxylates produced here, which contain, as alcohol component, the 3-hydroxymethyl-oxetane employed as starting material, are saponified in a further reaction step to oxetane-3-carboxylic acids (cf. German Patent Specification No. 1,907,117).

The oxetane-3-carboxylic acids of the formula (II) and salts thereof can also be prepared by a new process, by reacting 3-hydroxymethyl-oxetanes of the formula

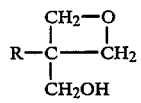  (III)

in which R has the abovementioned meaning,
with oxygen or oxygen-containing gases in aqueous alkaline medium at temperatures between 0° C. and the boiling point of the reaction mixture on a palladium and/or platinum catalyst, if appropriate in the presence of an activator, and then acidifying, if appropriate.

If, in the above process for the preparation of oxetane-3-carboxylic acids, 3-methyl-3-hydroxymethyloxetane is used as starting material, oxygen as oxidant, palladium and activated charcoal, with addition of bismuth nitrate, as catalyst, aqueous sodium hydroxide solution as reaction medium and dilute aqueous sulphuric acid for the acidification, then the course of the process may be illustrated by the following equation:

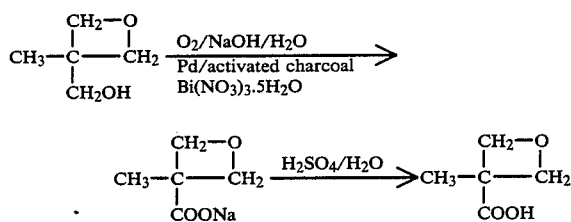

The 3-hydroxymethyl-oxetanes required as starting materials in the above process for the preparation of oxetane-3-carboxylic acids are generally defined by the formula (III). In this formula, R preferably has those meanings which have already been mentioned in connection with the description of the oxetane-3-carboxylic acids of the formula (II) as being preferred for this radical.

The following may be mentioned as examples of 3-hydroxymethyl-oxetanes of the formula (III): 3-methyl-3-hydroxymethyl-oxetane, 3-ethyl-3-hydroxymethyl-oxetane, 3-propyl-3-hydroxymethyl-oxetane, 3-isopropyl-3-hydroxymethyl-oxetane and 3-butyl-3-hydroxymethyl-oxetane, 3-hydroxymethyl-oxetane, 3-phenyl-3-hydroxymethyl-oxetane, 3-(4-chlorophenyl)-3-hydroxymethyl-oxetane and 3-cyclohexyl-3-hydroxymethyl-oxetane.

The 3-hydroxymethyl-oxetanes of the formula (III) are known or can be prepared in a simple fashion by known methods (cf. Houben-Weyl "Methoden der organischen Chemie" [Methods of Organic Chemistry], 4th edition, vol. VI/3, page 493 ff, Georg Thieme Verlag, Stuttgart 1965). Thus, 3-hydroxymethyl-oxetanes of the formula (III) can be obtained, for example, by cleaving carbon dioxide from the appropriate cyclic carbonates.

When carrying out the above process for the preparation of oxetane-3-carboxylic acids, suitable catalysts are all conventional palladium and platinum catalysts, and also their mixtures. The catalysts can additionally be combined with activators or mixtures of different activators. Suitable activators here are preferably lead, bismuth, lead compounds and bismuth compounds, and also their mixtures.

When carrying out the new process for the preparation of oxetane-3-carboxylic acids of the formula (II), the platinum or palladium, or mixtures which contain these metals, to be used as catalyst can be employed in a conventional fashion. Thus, the substances can be added in elemental form, for example as so-called platinum or palladium black, if appropriate in combination with other platinum-group metals, or alternatively in the form of compounds, such as, for example, the oxides.

The platinum or the palladium can alternatively be applied to a support. Suitable supports are, for example, activated charcoal, graphite, kieselguhr, silica gel, spinels, aluminum oxide, asbestos, calcium carbonate, barium sulphate or alternatively organic support materials.

Activated charcoals, for example so-called medicinal charcoals or activated charcoals produced from wood, as are often used for decolorization purposes, are preferably employed as support material.

The platinum and/or palladium content of the supported catalysts can be varied within a relatively wide range. In general, supported catalysts are used in which the content of these metals is between 0.01 and 20% by weight, preferably between 0.1 and 15% by weight.

The amounts in which the platinum and/or palladium catalysts are employed can also be varied within a relatively wide range. The amounts depend, inter alia, on the desired oxidation rate. In general, the amount of catalyst is selected so that beween 0.01 and 20 g, preferably between 0.05 and 10 g, of platinum and/or palladium are present per mole of 3-hydroxymethyl-oxetane of the formula (III) in the reaction mixture.

When carrying out the above process, it is also possible to employ a combination of platinum and palladium as catalyst.

The activity and/or selectivity of the platinum catalysts is considerably increased in the above process by the presence as activator of lead and/or bismuth and/or their compounds.

Even without addition of the abovementioned activators, palladium catalysts have such a surprisingly high activity and selectivity that, when using them, the addition of the abovementioned activators can sometimes be dispensed with.

The addition of the abovementioned activators also has a positive effect on the reusability of the catalysts.

The amounts in which these activators are employed, if appropriate, when carrying out the above process may be varied within a relatively wide range. The activator action is noticeable at added amounts as small as $5 \times 10^{-6}$ mole of metal or metal compound per mole of 3-hydroxymethyl-oxetane. 0.1 mole or more of activator may also be employed per mole of 3-hydroxymethyl-oxetane, but these greater added amounts do not generally offer an advantage. The activators are conventionally added in amounts from about $1 \times 10^{-5}$ to $1 \times 10^{-1}$ mole, preferably $2 \times 10^{-5}$ to $2 \times 10^{-2}$ mol, per mole of the 3-hydroxymethyl-oxetane to be oxidized.

The metals to be used, if appropriate, as activators when carrying out the above process may be employed in elemental form and/or in the form of their compounds, for example as oxides, hydroxides, hydrated oxides or oxo acids, or as salts of hydrogen acids, such as chlorides, bromides, iodides, sulphides, selenides and tellurides, or as salts of inorganicoxo acids, such as nitrates, nitrites, phosphites, phosphates, arsenites, arsenates, antimonites, antimonates, bismuthates, stannates, plumbates, selenites, selenates, tellurites, tellurates or borates, or as salts of oxo acids which originate from transition metals, such as vanadates, niobates, tantalates, chromates, molybdates, wolframates or permanganates, or as salts of organic aliphatic or aromatic acids, such as formates, acetates, propionates, benzoates, salicylates, lactates, mandelates, glyoxylates, oxetane-carboxylates, citrates or phenolates, or as complex compounds or as organometallic compound.

The activators may in each case be soluble, partially solluble or insoluble in the reaction mixture.

It is also possible to employ the activators in the above process in combination with other elements or compounds which are not claimed as activator.

The activators to be employed, if appropriate, when carrying out the above process may exist in different or in mixed valency states. Changes in valency may also occur during the reaction. If the activators are not already added as oxides and/or hydroxides, it is possible that they are totally or partially converted into these in alkaline medium. After the reaction, the platinum and/or palladium catalyst, with the activator (if this has remained undissolved), can be filtered off and used for further oxidation reactions. Losses of platinum or palladium catalyst and/or of activator should be replaced, if necessary.

The activator can be added to the reaction components as a solid, preferably in finely divided form, or in dissolved form. The activator can also be added as early as during the preparation of the platinum or palladium catalyst, or the platinum or palladium catalyst can be impregnated with the activator. The activator can also serve as support material for the platinum metal.

The oxidation by the above process is carried out in aqueous alkaline medium at a pH>7. The appropriate pH is set by addition of alkalis. Suitable alkalis are compounds of the alkali metals and/or alkaline earth metals, such as the hydroxides, carbonates, bicarbonates, phosphates and borates. The hydroxides and/or carbonates of sodium and/or potassium are preferably employed as alkali.

Since 1 mole of alkali OH$^{\ominus}$) are consumed per mole of acid formed during the above process, the amount of alkali to be employed is about 1 mole of alkali per mole of 3-hydroxymethyl-oxetane. In general, about 1 to 1.5 moles of alkali are employed per mole of 3-hydroxymethyloxetane.

Higher ratios can be used, but usually bring no significant advantages. If it is desired that only part of the 3-hydroxymethyl-oxetane employed is oxidized to oxetane-3-carboxylic acid, correspondingly less alkali may also be employed.

The alkali may be added to the reaction mixture all at once at the beginning of the reaction, or alternatively in batches or continuously during the reaction.

The 3-hydroxymethyl-oxetanes are preferably oxidized in aqueous solution. However, other inert organic substances, for example solvents, such as tert.-butanol, acetone, dioxane and/or toluene may also be present. The 3-hydroxymethyl-oxetanes are generally employed in the form of a 2 to 40% strength solution. Which concentration is expedient depends, inter alia, on the desired reaction rate. The latter decreases gradually at relatively high 3-hydroxymethyl-oxetane concentrations. It is also possible to oxidize mixtures of different 3-hydroxymethyloxetanes.

The reaction temperatures may be varied within a relatively wide range when carrying out the above oxidation process. Thus, the reaction temperature may be between the solidification point and the boiling point of the reaction mixture. The reaction temperature to be used in an individual case depends, inter alia, on the catalyst system, the amount of catalyst, the alkali concentration, the substance properties of the educts and products, and on the technical conditions, such as, for example, the desired reaction rate or heat dissipation. In general, the process is carried out at temperatures between 0° C. and the boiling point of the reaction mixture, preferably between 40° C. and 100° C.

Any sequence can be used for mixing together the platinum and/or palladium catalyst, and, if appropriate, activator, aqueous alkali and 3-hydroxymethyl-oxetane. Thus, the paltinum and/or palladium catalyst, and, if appropriate, activator, can be added to the mixture or solution of aqueous alkali and 3-hydroxymethyl-oxetane. Alternatively, the mixture of aqueous alkali and 3-hydroxymethyl-oxetane can be added to the platinum and/or palladium catalyst and, if appropriate, activator.

Finally, it is also possible to add 3-hydroxymethyl-oxetane, together with the remaining alkali, to the platinum and/or palladium catalyst, part of the aqueous alkali, and, if appropriate, activator. Furthermore, it is possible to add the activator to the mixture of the other components.

In general, the above oxidation process is carried out in such a fashion that oxygen or oxygen-containing gases, such as air, are brought into intimate contact with the reaction mixture, which contains aqueous alkali, the platinum and/or palladium catalyst, if appropriate activator, and 3-hydroxymethyl-oxetane. The catalyst need not be present in the reaction mixture suspended as a powder, but can instead be arranged in granular form as a fixed bed through which the other components flow.

When carrying out the above oxidation process, the pressure may be varied within a relatively wide range. In general, the process is carried out at pressures between 0.5 and 10 bar. The oxidation is preferably carried out at atmospheric pressure.

The course of the reaction can be followed by measuring the amount of oxygen taken up. The reaction is terminated when the amount of oxygen which is theoretically necessary for the preparation of the appropriate oxetane-3-carboxylic acid has been taken up. In general, the oxygen take-up ceases of its own accord at this stage, or slows down markedly.

When carrying out the above oxidation process, the reaction mixture is worked up by conventional methods. In general, a procedure is followed in which the catalyst and, if appropriate, an undissolved activator present, is separated off, for example by filtration. The alkali metal salt solutions of the oxetane-3-carboxylic acids obtained can be further used as such, if appropriate after prior concentration by evaporation. The alkali metal salt solutions of the oxetane-3-carboxylic acids can alternatively be evaporated completely, that is to say to dryness, and the salt residue remaining can be further used. If the free oxetane-3-carboxylic acids are to be prepared, a procedure is generally followed in which the reaction mixture remaining, if appropriate after prior concentration under reduced pressure, is acidified using dilute mineral acid, then extracted with an organic solvent which is sparingly soluble in water, and the organic phase, if appropriate after prior drying, is concentrated. Hydrochloric acid, sulphuric acid or phosphoric acid may preferably be employed here as mineral acids. Suitable organic solvents for the extraction are preferably ethers, such as diethyl ether and diisopropyl ether, furthermore ketones, such as methyl isobutyl ketone, and, in addition, optionally halogenated aliphatic or aromatic hydrocarbons, such as methylene chloride, chloroform, or toluene. It is also possible to liberate, on a cation exchanger, the respective oxetane-3-carboxylic acid from the aqueous alkali metal salt solutions produced initially, and to isolate them by gentle evaporation of the aqueous solution. If the conversion of 3-hydroxymethyl-oxetane used is incomplete, this can be removed before acidification by extraction of the aqueous alkali metal salt solution with an organic solvent which is sparingly soluble in water, recovered and, if appropriate, re-employed as starting material.

Suitable inorganic acid chlorides when carrying out the process according to the invention are all conventional inorganic acid chlorides. Thionyl chloride, phosphorus trichloride and phosphorus pentachloride may preferably be used.

All those compounds which are also known to catalyze the reaction of carboxylic acids and their salts with inorganic acid chlorides to form carboxylic acid chlorides (cf. Houben-Weyl, "Methoden der organischen Chemie" [Methods of Organic Chemistry], Georg-Thieme-Verlag, vol. VIII, pages 463 ff., Stuttgart 1952, and vol. E5, pages 593 ff (1985)) may be used as catalysts when carrying out the process according to the invention. Basic nitrogen compounds, such as tertiary amines and acid amines, may preferably be used. Pyridine and dimethylformamide may be mentioned as examples.

When carrying out the process according to the invention, the reaction temperatures may be varied within a relatively wide range. In general, the process is carried out at temperatures between 20° C. and the boiling point of the reaction mixture.

All conventional inert organic solvents may be used as diluents when carrying out the process according to the invention. Preferably suitable are aliphatic and aromatic, optionally chlorinated hydrocarbons, and also phosphoroxy chloride and carbon disulphide.

When carrying out the process according to the invention, a procedure is generally followed in which the oxetane-3-carboxylic acids, or salts thereof, are reacted with a stoichiometric amount, or alternatively with an excess, of inorganic acid chlorides, and if appropriate in the presence of a catalyst. The stoichiometric excess of inorganic acid chlorides here can be 5 to 300%. The catalyst is generally added in amounts from 0.1 to 20% by weight, relative to the oxetane-3-carboxylic acids, or metal salts thereof, employed.

The reaction mixture is heated until the reaction is complete, according to the heat and/or gas evolution. For better reaction control, the reaction can alternatively be carried out in the presence of an inert solvent. In general, the reaction mixture is heated to the reflux temperature and maintained at this temperature until the reaction is complete. The course of the reaction and the end of the reaction can be determined in a simple fashion by conventional methods, for example by gas chromatography.

The reaction mixture is worked up by conventional methods. In general, a procedure is followed in which the reaction mixture is subjected to a distillation. Unreacted inorganic acid chloride is collected separately during this and can be used for a further reaction. The distillations should be carried out, if appropriate, in vacuo or by incorporating a column.

2,2-Bis-chloromethyl-alkanoyl chlorides, which can be prepared by the process according to the invention, are valuable intermediates for the preparation of other substances. Thus, 2,2-bis-chloromethyl-alkanoyl chlorides of the formula (I) can be used as starting materials for the preparation of herbicidally active triazinone derivatives or for the synthesis of fungicidally active triazolyl derivatives.

For example, 2,2-bis-chloropivaloyl chloride, if appropriate after prior exchange of the chlorine atoms by fluorine atoms, can be converted, by reaction with trimethylsilyl cyanide, into the corresponding halogenopivaloyl cyanides, which can be converted to 1,2,4-triazin-5-one derivatives by known methods (cf. DE-OS (German Published Specification) 3,037,300).

Furthermore, for example, 2,2-bis-chloropivaloyl chloride can be converted, by treatment with potassium fluoride, into 2,2-bis-fluoropivaloyl fluoride, which reacts with magnesium monoethyl malonate to form 2,2-bis-fluoromethylbutan-3-one. The latter compound reacts with bromine to form 2,2-bis-fluoromethyl-4-bromo-butan-3-one, which, on reaction with 1,2,4-triazole, yields 2,2-bis-fluoromethyl-4-(1,2,4-triazol-1-yl)-butan-3-one. The latter can be converted into 2,2-bis-fluoromethyl-5-cyclohexyl-4-(1,2,4-triazol-1-yl)-pentan-3-ol by reaction with cyclohexylmethyl bromide and reduction of the product produced initially using sodium borohydride (cf. DE-OS (German Published Specification) 3,326,875, DE-OS (German Published Specification) 2,951,163 and JP-OS (Japanese Published Specification) 61,572 (1985). The reaction mentioned may be represented by the following equation:

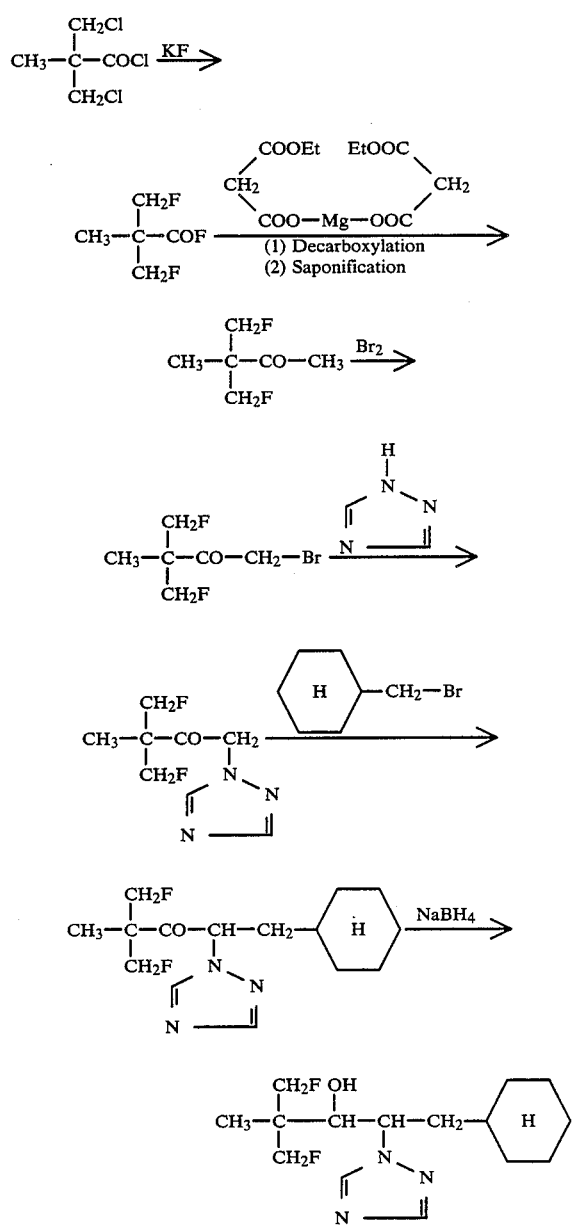

The execution of the process according to the invention is illustrated by the following examples.

EXAMPLE 1

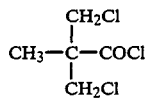

A mixture of 11.6 g (0.1 mol) of 3-methyl-oxetane-3-carboxylic acid, 35.7 g (0.3 mol) of thionyl chloride and 0.2 ml of dimethylformamide are heated slowly to the reflux temperature (about 120° C.), gas being evolved during the heating. The mixture is then stirred for a further 5 hours at this temperature. Examination of a sample by gas chromatography indicates that the 3-methyl-oxetane-3-carboxylic acid employed has reacted completely. Excess thionyl chloride is subsequently removed by distillation over a distillation bridge. The main fraction is distilled from the residue remaining at 70°–90° C. and a pressure of 10 mbar. 15.5 g of a product are obtained which, according to a gas chromatograph, is 96.1% 2,2-bis-chloromethyl-propanoyl chloride.

EXAMPLE 2

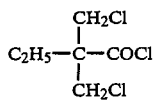

476 g (4 mol) of thionyl chloride are added dropwise to a mixture of 130 g (1 mol) of 3-ethyl-oxetane-3-carboxylic acid and 1 ml of dimethylformamide. The mixture is then heated to the reflux temperature at such a rate that a constant stream of waste gas is produced. The mixture is subsequently stirred at the reflux temperature. After a total of 32 hours, the mixture is distilled over a bridge. 166.6 g (0.82 mol) of 2,2-bis-chloromethyl-butanoyl chloride, which solidifies on standing at room temperature, are obtained in the boiling range from 95° to 120° C. at a pressure of 10 mbar.
melting point 38°–40° C.

Preparation of the starting material

EXAMPLE 3

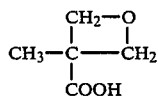

A solution of 20.4 g (0.2 mol) of 3-methyl-3-hydroxymethyl-oxetane in 100 ml (0.22 mol) of 2.2M aqueous Sodium hydroxide solution, 1 g of activated charcoal containing 5% by weight of palladium, and 0.03 g of $Bi(NO_3)_3.5H_2O$ are introduced into a reaction vessel fitted with stirrer, internal thermometer and gas inlet and the temperature of which is controlled by a heating mantle.

After expelling the air from the reaction vessel by means of oxygen, the stirrer is switched on and the reaction mixture is heated to 80° C. Oxygen under atmospheric pressure is passed into the mixture at this temperature. After 3 hours, 0.2 mol of oxygen has been taken up and the reaction ceases.

After filtering off the catalyst and washing with 20 ml of water, the filtrate is acidified to pH 1 using 50% strength sulphuric acid and extracted using 2×50 ml of methyl isobutyl ketone. After stripping the methyl isobutyl ketone at 60° C. in vacuo, 24 g of 3-methyl-oxetane-3-carboxylic acid remain as a residue which, according to a gas chromatogram, contains 3 to 4% of methyl isobutyl ketone, but otherwise no further impurities. The yield accordingly works out at 99% of theory. Melting point 58°–60° C. (after recrystallization from ligroin).

EXAMPLE 4

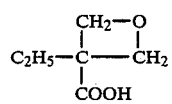

The procedure as in Example 3 is followed, but with the difference that 11.6 g (0.1 mol) of 3-ethyl-3-hydroxyethyl-oxetane are dissolved in 100 ml of 1.2M aqueous sodium hydroxide solution and, after addition of 1 g of activated charcoal containing 5% by weight of palladium, and 30 mg of $Bi(NO_3)_3.5H_2O$, are oxidized at 80° C. under atmospheric pressure using oxygen. After 90 minutes, 0.1 mol of oxygen has been taken up and the reaction ceases.

After filtering off the catalyst, extraction of the filtrate, adjusted to pH 1 using 50% strength sulphuric acid, with diethyl ether yields 12.9 g of a product which, according to a gas chromatogram, is 99.7% 3-ethyl-oxetane-3-carboxylic acid. The yield accordingly works out at 98.9% of theory.

Melting point 25° C.

EXAMPLE 5

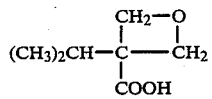

The procedure as in Example 3 is carried out, but with the difference that 13 g (0.1 mol) of 3-isopropyl-3-hydroxymethyl-oxetane in 100 ml of 1.2M aqueous sodium hydroxide solution are oxidized in the presence of 1 g of activated charcoal containing 5% by weight of palladium, and 30 mg of $Bi(NO_3)_3.5H_2O$. After 120 minutes, 0.1 mol of oxygen has been taken up, and the oxygen take-up has ceased.

After filtering off the catalyst, acidifying the filtrate to pH 1 and extracting with diethyl ether, 14.1 g of a product which is 94.5% 3-isopropyl-oxetane-3-carboxylic acid and 3.3% 3-isopropyl-3-hydroxymethyl-oxetane remain after concentrating the organic phase under reduced pressure. The yield (selectivity), relative to reacted starting material, accordingly works out at 96% of theory.

Melting point 52°–54° C.

It is understood that the specification and examples are illustrative but not limitative of the present invention and that other embodiments within the spirit and scope of the invention will suggest themselves to those skilled in the art.

We claim:

1. A process for the preparation of a 2,2-bis-chloromethylalkanecarboxylic acid chloride of the formula in which R is hydrogen, alkyl having 1 to 12 carbon atoms, cycloalkyl having 3 to 8 carbon atoms or phenyl which is optionally substituted by halogen and/or alkyl having 1 to 4 carbon atoms, which comprises reacting an oxetane-3-carboxylic acid of the formula

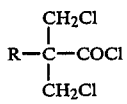

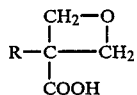

or a salt thereof, with an inorganic acid chloride at a temperature between 20° C. and the boiling point of the reaction mixture in the presence of pyridine or dimethylformamide as catalyst.

2. A process according to claim 1, wherein the oxetane-3-carboxylic acid is in the form of a salt.

3. A process according to claim 1, wherein the inorganic acid chloride is thionyl chloride, phosphorus trichloride or phosphorus pentachloride.

4. A process according to claim 1, wherein an aliphatic or aromatic, optionally chlorinated hydrocarbon, phosphoroxy chloride or carbon disulphide is employed as a diluent.

* * * * *